United States Patent [19]

Caskey et al.

[11] 4,415,753

[45] Nov. 15, 1983

[54] PROCESS FOR PREPARING P-AMINOPHENOL AND ALKYL SUBSTITUTED P-AMINOPHENOL

[75] Inventors: Douglas C. Caskey, O'Fallon; Douglas W. Chapman, St. Louis, both of Mo.

[73] Assignee: Mallinckrodt, Inc., St. Louis, Mo.

[21] Appl. No.: 343,993

[22] Filed: Jan. 29, 1982

[51] Int. Cl.$^3$ ............... C07C 85/11; C07C 89/00
[52] U.S. Cl. ................... 564/418; 564/112; 564/300
[58] Field of Search .............. 564/418, 112, 300

[56] References Cited

U.S. PATENT DOCUMENTS

| | | | |
|---|---|---|---|
| 3,383,416 | 5/1968 | Benner | 564/300 |
| 3,694,509 | 9/1972 | Rylander et al. | 564/300 |
| 3,715,397 | 2/1973 | Rylander et al. | 564/418 |
| 4,176,138 | 11/1979 | Sathe | 564/418 |
| 4,307,249 | 12/1981 | Derrenbacker | 564/418 |

FOREIGN PATENT DOCUMENTS 54-24837 of 1979 Japan .................... 564/300

*Primary Examiner*—John Doll
*Attorney, Agent, or Firm*—Senniger, Powers, Leavitt and Roedel

[57] ABSTRACT

A process for the production of unsubstituted and lower alkyl substituted p-aminophenols. A charge mixture is prepared comprising an unsubstituted or lower alkyl substituted nitrobenzene substrate, a platinum catalyst and a sulfur compound. The sulfur compound may be a divalent sulfur compound in which sulfur is bonded to two other moieties or a compound reducible to such sulfur compound under catalytic hydrogenation conditions. Hydrogen is introduced into the mixture while it is agitated at a temperature of 0°-40° C., thereby reducing the substrate to an unsubstituted or alkyl substituted phenylhydroxylamine. The hydroxylamine is thereafter heated to a temperature of at least 70° C. and agitated at at least 70° C. in the presence of a highly dissociated acid, thereby effecting rearrangement of the hydroxylamine to the corresponding p-aminophenol.

18 Claims, 3 Drawing Figures

PROCESS FOR PREPARING P-AMINOPHENOL AND ALKYL SUBSTITUTED P-AMINOPHENOL

BACKGROUND OF THE INVENTION

This invention relates to the field of synthesis of aminophenols and more particularly to an improved process for the preparation of substituted or unsubstituted p-aminophenol through the rearrangement of a hydroxylamine produced by partial hydrogenation of nitrobenzene.

In the conventional commercial process for manufacture of p-aminophenol, as described in Benner U.S. Pat. No. 3,383,416, nitrobenzene is catalytically hydrogenated in the presence of a dilute sulfuric acid solution. Under the conditions utilized in the Benner patent, the nitrobenzene is subject to complete reduction to aniline by reaction with three moles of hydrogen:

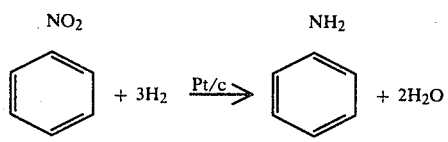

However, the intermediate phenylhydroxylamine, produced by reaction of nitrobenzene with two moles of hydrogen, is rapidly removed from the reaction zone by absorption into the sulfuric acid phase where it rearranges to p-aminophenol:

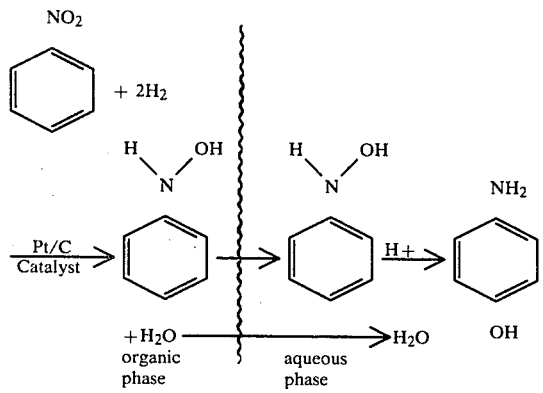

Fortuitously, the noble metal catalyst congregates in the nitrobenzene phase so that phenylhydroxylamine absorbed into the acid phase is essentially removed from the reaction zone, and conversion of phenylhydroxylamine to aniline is thereby inhibited. This feature also permits recovery of the catalyst in the nitrobenzene phase when the phases are permitted to separate so that, by terminating the reaction prior to the conversion of all of the nitrobenzene, the catalyst is easily recovered by decantation and recycled in its nitrobenzene vehicle for use in another batch or in an earlier stage of a cascade continuous hydrogenation system.

Despite its numerous salutary features, the Benner process does not entirely avoid conversion of phenylhydroxylamine to aniline. Thus, typically the yield of p-aminophenol is about 75% while 15% of the nitrobenzene is converted to aniline. The amount of byproduct aniline obtained can be minimized by lowering the reaction rate but this, of course, involves a sacrifice in productivity.

Rylander et al., U.S. Pat. No. 3,694,509 describes a method for producing arylhydroxylamines while minimizing the fraction of arylamines that are produced prior to the uptake of two moles of hydrogen per mole of substrate. Rylander et al achieve this improvement by incorporating from 0.1 to 100 mols dimethyl sulfoxide per mole of catalyst metal in the reactor charge mixture. However, Rylander et al.'s disclosure is concerned only with the preparation of arylhydroxylamines and contains no teaching relevant to the production of p-aminophenol by catalytic hydrogenation or otherwise.

Rylander et al. U.S. Pat. No. 3,715,397 discloses a process for preparation of p-aminophenol by catalytic hydrogenation of nitrobenzene in a sulfuric acid system in the presence of DMSO, using a platinum oxide catalyst. Phenylhydroxylamine produced in the hydrogenation is converted in situ to p-aminophenol. The acid strength is that obtained by mixing 25 ml concentrated sulfuric acid with 75 ml water. Reaction is carried out in a batch system until absorption of 2 moles of $H_2$ per mole of nitrobenzene.

Japanese Pat. No. 54[1979]-24837 discloses a process for producing arylhydroxylamines by catalytic hydrogenation of substituted or unsubstituted nitrobenzene in a solvent containing phosphoric acid, its alkali metal salts, an ester phosphite, an ester thiophosphite, an alkyl or aryl phosphine, an alkyl or aryl aminophosphine, an alkyl or aryl sulfide, a carboalkoxy alkyl sulfide, an alkyl or aryl mercaptan or thiophene.

SUMMARY OF THE INVENTION

Among the several objects of the present invention, may be noted the provision of an improved process for the manufacture of p-aminophenol by catalytic hydrogenation of nitrobenzene or an alkyl substituted nitrobenzene; the provision of such a process which minimizes the formation of by-product aniline; the provision of such a process which maximizes the quality of the product obtained, and the provision of such a process which can be operated to provide improved yields and quality without sacrifice in productivity.

Briefly, therefore, the present invention is directed to a process for the production of a substituted or unsubstituted p-aminophenol having the formula

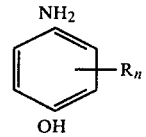

where R is lower alkyl and n is 0, 1 or 2. In the process, a charge mixture is prepared comprising a substituted or unsubstituted nitrobenzene substrate having the formula

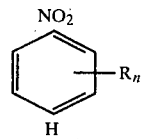

where R and n are as defined above, a catalyst containing platinum, and a divalent sulfur compound in which sulfur is bonded to two other moieties or a compound reducible to such divalent sulfur compound under catalytic hydrogenation conditions. Hydrogen is introduced into the charge mixture while it is agitated at a temperature of between about 0 and about 40° C., thereby reducing the substrate to a hydroxylamine having the formula

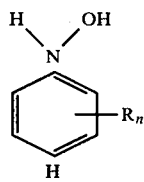

where R and n are as defined above. Thereafter the hydroxylamine is heated to a temperature of at least about 70° C. and agitated at at least 70° C. in the presence of a highly dissociated acid, thereby effecting its rearrangement to the corresponding p-aminophenol.

Other objects and features will be in part apparent and in part pointed out hereinafter.

BRIEF DESCRIPTION OF THE DRAWINGS

Corresponding reference characters indicate corresponding parts in the several views of the drawings.

DESCRIPTION OF THE PREFERRED EMBODIMENT

Figure 1:
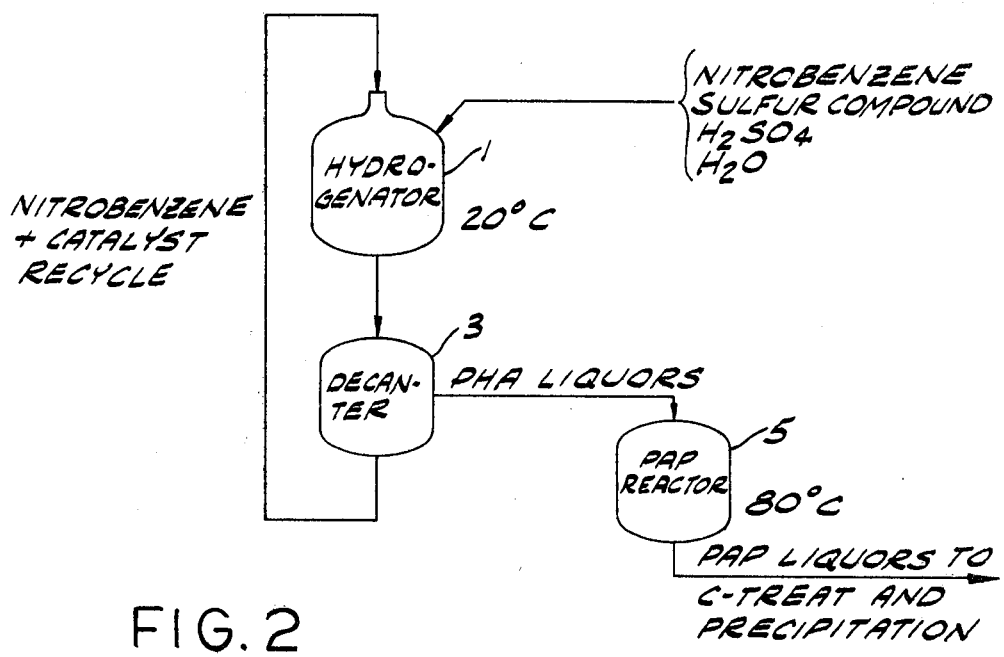
FIG. 1 is a schematic flow sheet illustrating an embodiment of the process of the invention in which acid is charged to the hydrogenator.

In accordance with the present invention, it has been found that formation of byproduct aniline can be essentially eliminated, yields of p-aminophenol improved and product quality enhanced by the combined effect of several significant features of a novel process for manufacture of p-aminophenol. Thus, by modifying the catalyst system through incorporation of certain sulfur compounds in the hydrogenator charge mixture, conversion of phenylhydroxylamine to byproduct aniline is essentially eliminated.

Low temperature hydrogenation thus affords the further opportunity to conduct the hydrogenation and rearrangement steps in separate vessels so that the parameters of the hydrogenation step can be manipulated independently of the rearrangement, for optimal performance in both steps. In accordance with the invention, therefore, it has been discovered that hydrogenation can either be carried out in the presence of an aqueous acid phase, as in the conventional Benner process, or in a solvent system. Where the hydrogenation reaction charge mixture contains acid, the phenylhydroxylamine product is absorbed into the aqueous phase as a salt. Subsequently, the aqueous phase may be heated for the rearrangement to p-aminophenol. In the solvent system, the solvent is stripped off and the phenylhydroxylamine is contacted with an acid in a vessel separate from the hydrogenation vessel.

In either case, low temperature hydrogenation without conversion to aniline is afforded by use of a modified catalyst system in which the charge mixture to the hydrogenation vessel contains a sulfur compound which enhances the selectivity of the catalyst for converting nitrobenzene to phenylhydroxylamine and inhibiting the conversion to aniline. Generally, it has been discovered that the sulfur compounds which are the most effective agents for enhancing catalyst selectivity are divalent sulfur compounds in which sulfur is bonded to two other moieties, particularly dialkyl sulfides such as, for example, dimethyl sulfide, ethyl propyl sulfide, bis(dodecyl)sulfide and methyl octyl sulfide. Other such compounds include thiols, hydrogen sulfide and thiophene. Alternatively, the sulfur compound may be one which is reducible to a divalent sulfur compound under catalytic hydrogenation conditions. Prominent among the latter classification of selectivity enhancing agents are dimethyl sulfoxide and other dialkyl sulfoxides. In addition to dialkyl sulfides and sulfoxides, other sulfur compounds useful in the process of the invention include diaryl sulfides, aryl alkyl sulfides, the corresponding sulfoxides, and thiols.

The process of the invention is applicable to substituted as well as unsubstituted nitrobenzene. In particular, it has been found the process is applicable to the conversion to the corresponding p-aminophenol of substrates having the general formula

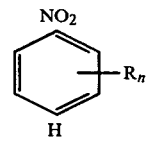

where R is lower alkyl and n is 0, 1 or 2. Typical of substituted nitrobenzene subtrates are o-nitrotoluene, m-nitrotoluene and 2,6 dimethylnitrobenzene. On hydrogenation the substrate is converted to the hydroxylamine

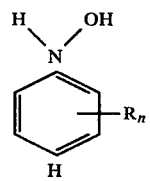

and, upon subsequent rearrangement by contact with acid, the hydroxylamine isomerizes to the corresponding p-aminophenol

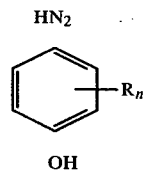

In each instance, R and n are as defined above.

A variety of dilute highly dissociated acids can be used for the rearrangement step, with sulfuric acid being preferred. Other exemplary acids include phosphoric, alkylsulfonic, arylsulfonic (such as benzenesulfonic and toluenesulfonic) and trihaloacetic. Hydrogen halide acids are preferably not used.

Illustrated in FIG. 1 is a schematic flow sheet of an embodiment of the invention in which nitrobenzene is reduced to phenylhydroxylamine in the presence of sulfuric acid. Nitrobenzene, sulfuric acid, water, a sulfur compound and catalyst are charged to a hydrogenation reactor vessel 1, the reactor purged with nitrogen or other inert gas to displace oxygen from the headspace, and then purged with hydrogen to eliminate the inert gas. Hydrogen pressure is applied and reaction carried out by agitation of the reacting mixture at a temperature in the range of 0° to 40° C., preferably 15°-20° C. Exothermic reaction heat is removed and the reaction temperature controlled by cooling water passed through a jacket, coil or external heat exchanger for the reactor. Nitrobenzene is readily reduced to phenylhydroxylamine but the presence of the sulfur compound inhibits conversion of phenylhydroxylamine to aniline and, as the phenylhydroxylamine is formed, it is absorbed into the acid phase forming the sulfate salt. The reaction is preferably terminated after 60-90% of the nitrobenzene is converted to phenylhydroxylamine, after which the batch is blown to a decant tank 3 in which the nitrobenzene and aqueous sulfuric acid phases are allowed to separate. The nitrobenzene phase contains the catalyst and is recycled to vessel 1 as a part of the charge to the next batch. The aqueous acid (phenylhydroxylamine liquor) phase is transferred to a rearrangement reactor 5 in which it is agitated at a temperature of at least about 70° C., preferably about 80° C., for conversion of the phenylhydroxylamine sulfate salt to p-aminophenol.

While the two reaction steps may be operated either on a batch or continuous basis, it may be desirable to feed the rearrangement reactor continuously and use the heat from the exothermic rearrangement reaction to bring the feed up to reaction temperature. P-aminophenol liquors removed from the rearrangement reactor are subsequently subjected to conventional carbon treatment and precipitation steps for purification and recovery of the final product.

The dilute sulfuric acid solution used in the process of FIG. 1 typically has substantially the same composition as disclosed in the Benner patent, i.e., 5-20% by weight, preferably 10-15% by weight. For purposes of the rearrangement reaction, there should be 1.0 to 5.0 equivalents of acid per mol of phenylhydroxylamine, preferably 1.75 to 2.25 equivalents of acid per mole.

Platinum is used as the catalyst in the partial hydrogenation reaction. Preferably the catalyst is provided on a carbon support at a level of approximately 0.5-5% by weight platinum. Other acid resistant supports may also be used. Platinum oxide catalysts can be used but platinum metal is preferred.

Catalyst loading is also a parameter of some importance in the process of the invention. Preferably the charge mixture contains between about $3.0 \times 10^{-5}$ and about $5.0 \times 10^{-4}$ gram-atom platinum per mole of substrate.

Where a dialkyl sulfoxide such as dimethyl sulfoxide is used as the sulfur compound in the charge mixture to a batch hydrogenation, it has been found that best results are achieved at a sulfur compound concentration greater than 100 moles per gram atom of platinum metal. Generally, the sulfoxide compound concentration falls in the range of between about 150 and about 400 moles per gram atom catalyst, with approximately 300 moles per gram atom being most preferred. In continuous operation, however, much lower levels dimethyl sulfoxide, typically 0.5 to 20 moles/gram-atom platinum are used so as to avoid accumulation of dimethyl sulfide in the head space of the reactor.

Where a dialkyl sulfide, aryl alkyl sulfide, or thiol is used as the sulfur compound, it has been found that the required dosages are much lower than in the case of a sulfoxide. This finding suggests that the sulfide is the operative agent for control of catalyst activity and selectivity, and that the sulfoxides are effective to the extent that they are converted to the sulfides under catalytic hydrogenation conditions. Thus, where sulfide is initially supplied to the charge mixture, its range of concentrations and optimum concentration are less than 5% of those specified for the sulfoxides, i.e., between about 0.1 and about 10 moles per gram atom of platinum.

Although reaction in the preferred range of 15°-20° C. adversely affects the reaction kinetics as compared to conventional hydrogenation at 80° C., this may be compensated for by a modest increase in the hydrogen pressure. Thus, reaction proceeds satisfactorily with a hydrogen pressure of 25-200 psig while, by comparison, the Benner process typically operates at pressures in the 0-20 psig range. In order to maximize the reaction rate at a given available hydrogen pressure, it is desirable to provide for both maximum feasible cooling capacity and vigorous agitation since hydrogen introduction is normally limited by heat removal capacity during the early portion of the cycle, and the reaction rate is limited by mass transfer rates during the later portion.

Figure 2:
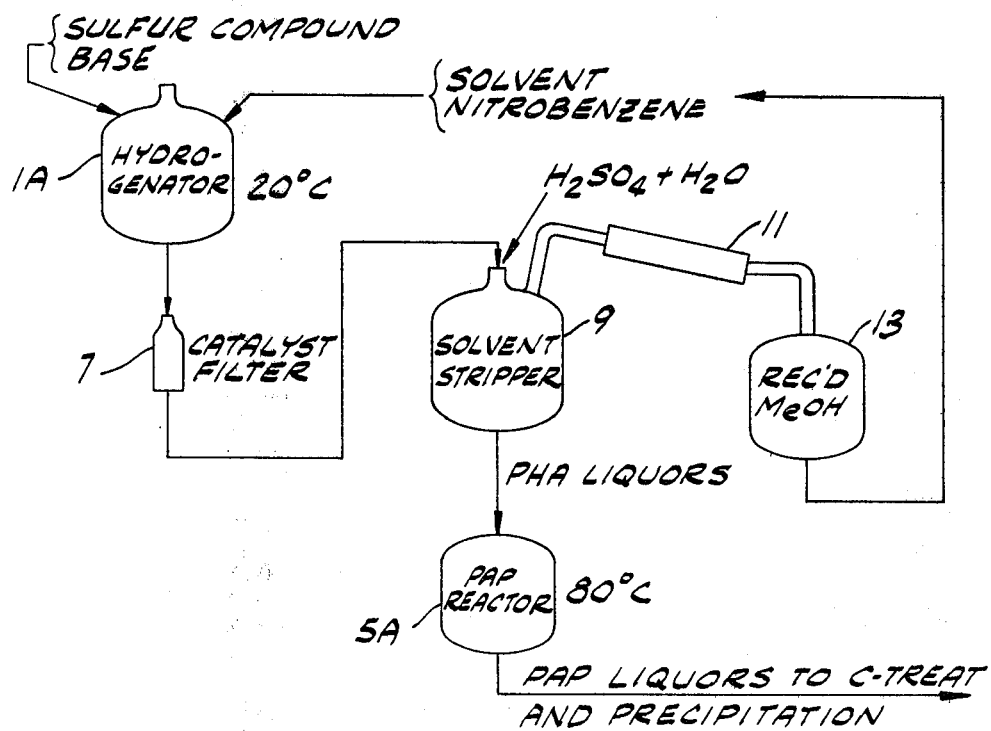
FIG. 2 is a schematic flow sheet illustrating an embodiment in which a substituted or unsubstituted phenylhydroxylamine is prepared by hydrogenation of the corresponding nitrobenzene in a solvent system.

In an alternative embodiment of the invention illustrated in FIG. 2, phenylhydroxylamine is produced by partial hydrogenation of nitrobenzene in a solvent system, and the phenylhydroxylamine product is rearranged to p-aminophenol after removal of the solvent from the reaction mixture by stripping. In the solvent process, nitrobenzene, solvent, sulfur compound and a catalyst are charged to a hydrogenation reactor 1A. The reactor is purged in the same manner as in the process of FIG. 1, and hydrogenation is carried out by vigorous agitation at 0°-40° C., preferably 15°-20° C. and a hydrogen pressure of 25-200 psig. The reaction is carried substantially to quantitative conversion of nitrobenzene to phenylhydroxylamine after which the batch is blown to a solvent stripper vessel 9 via a filter 7 in which the catalyst is removed. Since there is only a single liquid phase, catalyst is not removed in a nitrobenzene phase as in the Benner process. By application of heat and vacuum at stripper 9, the solvent is removed from the reaction mixture as a vapor, after which it is condensed in a condenser 11, collected in a receiver 13, and recycled for use in subsequent hydrogenation batches. To minimize product degradation, stripping should be carried out under vacuum sufficient to maintain the still pot temperature at 60° C. or below. Bottoms from the stripper comprise phenylhydroxylamine and are delivered to a rearrangement reactor 5A where they are contacted with dilute sulfuric acid solution and the phenylhydroxylamine rearranged to p-aminophenol. Conditions in the rearrangement step are essentially identical to those utilized in the process illustrated in FIG. 1. P-aminophenol liquors leaving reactor 5A are subjected to conventional carbon treatment and precipitation steps for the purification and recovery of the p-aminophenol.

In the solvent process of FIG. 2, further significant improvement in catalyst selectivity control may be achieved by the use of a basic medium rather than the neutral medium used in the DMSO modified catalyst system taught in the Rylander et al. patent. Where the medium is basic and contains a sulfur compound of the aforesaid type, quantitative conversion to phenylhydroxylamine can be effected without significant aniline formation since the reaction terminates spontaneously upon the uptake of two moles of hydrogen per mole of nitrobenzene. Accordingly, the reaction end point is not only controlled but readily identified by the cessation of hydrogen flow into the hydrogenator.

However, not all bases are of equal value in creating favorable conditions for the partial hydrogenation reaction. Most preferred are ammonia and aliphatic amines. Primary, secondary, and tertiary amines are all suitable. Phosphite esters such as triethyl phosphite are also suitable, while phosphine and various organic phosphines, including aliphatic and aryl phosphines, can also be used but are preferably avoided because of their toxicity. Arsines are also believed to be effective but are extremely toxic and would normally not be used.

Because of the cooperative effect of the sulfur compound and the base, the optimum proportion of base varies with the proportion of sulfur compound in the charge mixture. Generally, it is preferred that the mixture contain between about 100 and about 300 moles of base per gram atom of platinum in the mixture. At most sulfur compound concentrations, further increases in base concentration have a positive but relatively slight effect on selectivity. However, there is typically an optimum proportion of sulfur compound at which essentially 100% selectivity can be achieved at only a very modest base concentration, for example, 50–100 moles per gram-atom of platinum (see FIG. 3). Because selectivity is adversely affected by sulfur compound concentrations in excess of the optimum, the relationship between sulfur compound and base makes it possible and desirable to adopt a process control strategy in which sulfur compound is charged to a level short of the optimum and base additive is used as a vernier to adjust to a combination that provides optimum performance. Some excess of base has no adverse effect on selectivity. Moreover, in the case of ammonia, any significant excess can be removed by degassing the batch through inert gas purging or application of vacuum.

As the solvent for the charge mixture, methanol is preferred, but other lower alcohols are satisfactory. Ethers, including cyclic ethers such as tetrahydrofuran are generally useful, as are carboxylic acid esters. While the use of a solvent is essential to prevent precipitation of phenylhydroxylamine from the reaction mixture, the process is preferably operated with a charge mixture that produces a hydrogenation reaction mixture close to the point of saturation so as to maximize reactor payload and reduce both solvent losses and the energy and other operational costs of recovery.

Because a solvent rather than an acid system is used in the process of FIG. 2, a somewhat broader range of catalyst supports can be used. Supports such as alumina, for example, are suitable.

The following examples illustrate the invention.

EXAMPLE 1

Phenylhydroxylamine was prepared by catalytic hydrogenation of nitrobenzene in a stirred 1 liter steel pressure reactor having an automatic temperature controller. Temperature of the reaction was monitored by a thermocouple and cooling effected by cooling water passed through internal coils. A heating mantle was provided for heating of the contents of the reactor when necessary.

A reaction charge mixture was prepared by adding to the reactor nitrobenzene (150 ml), 3% platinum on carbon catalyst (5.55 grams; 70% wet) methanol solvent (250 ml) dimethyl sulfoxide (4.00 grams) and 30% aqueous ammonia (1.35 grams).

After charging was completed the reactor was purged with nitrogen, then with hydrogen and pressurized with hydrogen to 140 psig. Reaction was commenced by starting the agitator and temperature was controlled during the reaction in the range of 18° to 20° C. Hydrogen uptake was monitored with a rotameter and hydrogen absorption terminated after slightly more than 2.00 moles hydrogen per mole nitrobenzene was consumed. At this point the hydrogen uptake stopped spontaneously and abruptly, signaling the end of the reduction.

After the reaction terminated, the reactor was purged with nitrogen, the reaction mixture was removed from the autoclave and the catalyst was separated from the reaction mixture by filtration. The phenylhydroxylamine liquor filtrate obtained was adapted to be heated to a temperature of 70° C. to cause the phenylhydroxylamine therein to isomerize to p-aminophenol.

EXAMPLES 2–16

Using the apparatus and method generally described in Example 1, a series of runs were made in which phenylhydroxylamine was produced by catalytic hydrogenation of nitrobenzene in the presence of a sulfur compound and a base. For each run, the time of the hydrogenation reaction was recorded and the selectivity was calculated. Selectivity is defined as the ratio of moles of phenylhydroxylamine produced to moles of nitrobenzene reacted times 100. Results of the runs of these Examples are set forth in Table I. Except when shown differently in this table, components of the reactor charge mixtures were the same as for Example 1.

TABLE 1

| Example # | moles Modifier g-atom Pt | Catalyst wgt., g. | Pressure, H2 psig | Time, min. | Selectivity |
|---|---|---|---|---|---|
| 2 | 68 DMSO, 94 NH$_3$ | 1.39 g | 100 | 205 | 81.4 |
| 3 | 68 DMSO, 94 NH$_3$ | 2.78 | 100 | 115 | 87.5 |
| 4 | 136 DMSO, 185 NH$_3$ | 2.78 | 100 | 128 | 88.4 |
| 5 | 200 DMSO, 185 NH$_3$ | 2.78 | 100 | 140 | 90.7 |
| 6 | 400 DMSO, 185 NH$_3$ | 2.78 | 140 | 120 | 92.4 |
| 7 | 400 DMSO | 2.78 | 100 | 160 | 89.3 |
| 8 | 136 DMSO, 186 NH(CH$_3$)$_2$ | 2.78 | 100 | 127 | 90.9 |
| 9 | 136 DMSO | 2.78 | 100 | 116 | 80.5 |
| 10 | 10 S(CH$_3$)$_2$, 185 NH$_3$ | 2.78 | 100 | 128 | 92.4 |
| 11 | 158 S(CH$_3$)$_2$, 185 NH$_3$ | 2.78 | 100 | 183 | 91.7 |
| 12 | 1.4 S(CH$_3$)$_2$, 185 NH$_3$ | 2.78 | 100 | 85 | 84.2 |

TABLE 1-continued

| Example # | moles Modifier g-atom Pt | Catalyst wgt., g. | Pressure, H2 psig | Time, min. | Selectivity |
|---|---|---|---|---|---|
| 13 | 1.0 S(C$_2$H$_5$)$_2$, 185 NH$_3$ | 2.78 | 100 | 91 | 84.4 |
| 14 | 0.2 CH$_3$CH$_2$CH$_2$CH$_2$SH 185 NH$_3$ | 2.78 | 100 | 165 | 77.6 |
| 15 | .09 (CH$_3$)CHSSCH(CH$_3$)$_2$ 185 NH$_3$ | 2.78 | 100 | 187 | 86.4 |
| 16 | 136 DMSO, 186 N(C$_2$H$_5$)$_3$ | 2.78 | 100 | 127 | 90.9 |

EXAMPLE 17

Using the apparatus and method described in Example 1, a series of runs were made in which phenylhydroxylamine was produced by catalytic hydrogenation of nitrobenzene in the presence of dimethyl sulfoxide and ammonia. Proportions of DMSO and ammonia were varied to establish a statistical basis for determining catalyst selectivity as a function of the two catalyst modifying components. Data obtained from this series of runs was subjected to mathematical analysis which yielded a series of catalyst selectivity contours on an ammonia versus DMSO grid. These contours are plotted in FIG. 3.

Figure 3:
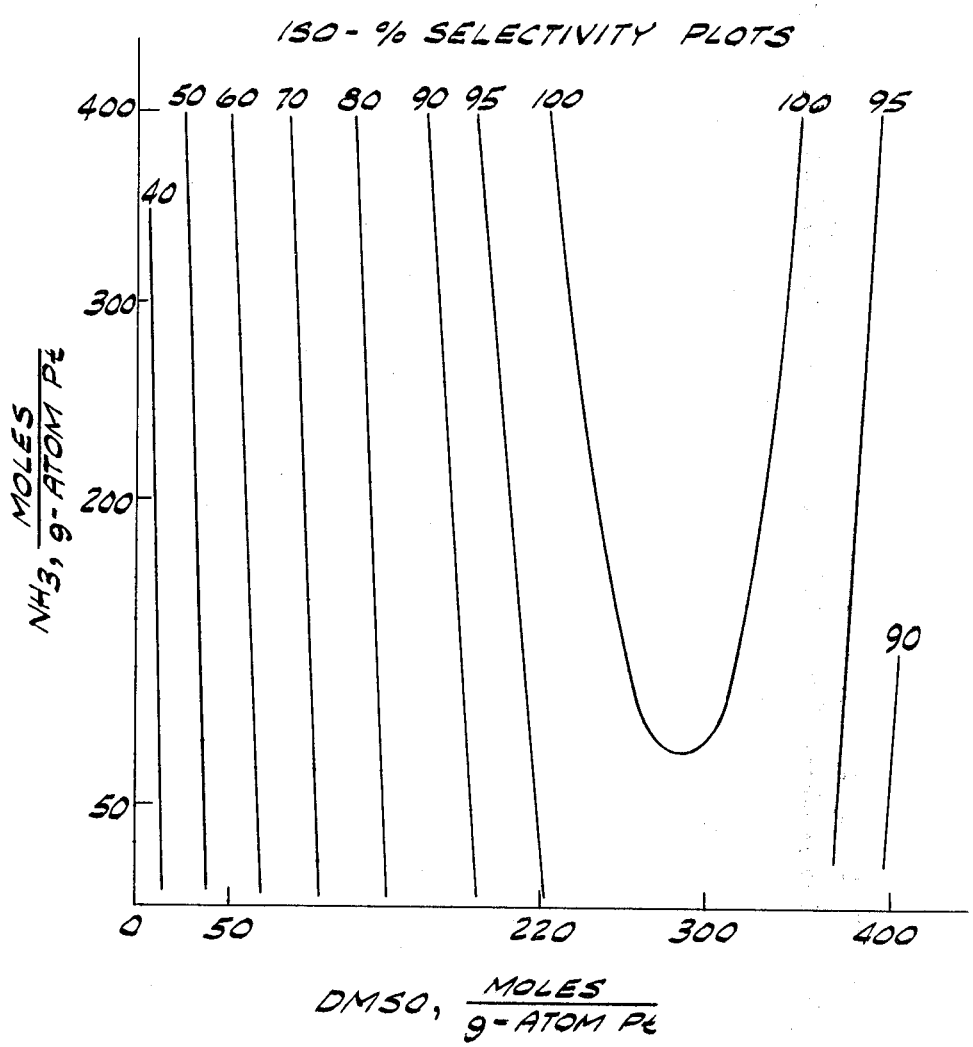
FIG. 3 is an exemplary plot of catalyst selectivity contours for different combinations of dimethyl sulfoxide and $NH_3$ in the solvent system hydrogenation of nitrobenzene to phenylhydroxylamine.

It may be seen that plots such as FIG. 3 provide a basis for process control through a strategy of establishing a base level of DMSO and adjusting ammonia level. Catalyst selectivity is maximized at an optimum locus of combinations of DMSO and base represented by the contour labeled 100% in FIG. 3. Typically, DMSO is incorporated in the charge mixture at a level lower than what the optimum sulfur compound content would be at zero ammonia content, and the ammonia content adjusted to provide a combination on or near the optimum locus. In the instance of FIG. 3, approximately 200-260 moles DMSO per gram atom of platinum may be advantageously incorporated in the charge mixture and the ammonia level adjusted to between about 50 and about 300 moles per gram atom to achieve a combination on or near the aforesaid locus.

EXAMPLE 18

To a one liter stainless steel pressure reactor were charged:
  o-nitrotoluene (116 g; 0.85 gram-moles)
  methanol (300 ml)
  dimethyl sulfoxide (1.34 g; 0.0172 moles)
  concentrated aqueous ammonia (1.35 g; 0.0238 moles)
  3% platinum on carbon catalyst, 70% wet (2.78 grams).

The temperature of the charge mixture was adjusted to 15 to 20° C. after which the reactor was sealed, purged with nitrogen and then purged with hydrogen. After purging, the reactor was pressurized with hydrogen to 100 psig and rapid agitation was commenced to start the reaction. By passage of cooling water through coils inside the reactor, the internal temperature was maintained at 15°-20° C. throughout the reaction. After slightly more than 2.00 moles hydrogen per mole of nitrogen compound had been absorbed, the hydrogen flow rate dropped essentially to zero. At that point, the reactor was purged with nitrogen and disassembled and the reaction mixture filtered to recover the catalyst.

Water (752 ml) and concentrated sulfuric acid (48 ml) were charged to a three-neck, two liter flask equipped with a dropping funnel, a take-off arm condenser and receiver, thermometer, multi-speed agitator and nitrogen purgation system. The filtered reduction liquor from the hydrogenation step was charged to the dropping funnel after which the entire system was purged with nitrogen and the aqueous sulfuric acid solution in the flask was heated to 85°-90° C. While a slow nitrogen purge was continued and the temperature of the dilute acid was maintained at 85°-95° C., the reduction liquors were slowly delivered from the dropping funnel into the hot acid solution. As the addition proceeded, methanol was distilled off, condensed and recovered. After the acid and phenylhydroxylamine liquor were stirred for one hour, the mixture was cooled to 10° C. and aqueous ammonia added to a final pH of 7.5-8.0, thus precipitating 3-methyl-4-aminophenol produced by rearrangement of the o-methylphenylhydroxylamine produced in the reaction step. The resultant slurry was filtered at 10° C. to recover the product which was then washed with 80 ml water. Dry weight of the product was 68.8 g., equivalent to about 66% of theory yield.

EXAMPLE 19

Using the apparatus and method described in example 18, p-aminophenol was produced from nitrobenzene. The charge mixture comprised:
  nitrobenzene (180 g; 1.46 mole)
  isopropanol (350 ml)
  dimethyl sulfoxide (1.34 g; 0.0172 moles)
  concentrated aqueous ammonia (1.35 g; 0.0238 moles)
  3% platinum on carbon catalyst, 70% wet (3.5 g; 0.000162 gram-atoms platinum)

The dilute acid solution charge to the rearrangment reaction flask comprised water (2719 ml) and concentrated sulfuric acid (164 ml). The rearrangement reaction was conducted under a vacuum of 200 mm Hg in order to promote the stripping of the isopropanol from the reacting mixture.

Dry weight of the p-aminophenol product obtained was 106 g, equivalent to approximately 67% theory yield.

EXAMPLE 20

To a 1 liter stainless steel pressure reactor were charged:

| | |
|---|---|
| water | 375 ml. |
| concentrated sulfuric acid | 48 ml.; 0.90 moles |
| nitrobenzene | 23 ml; 0.224 moles |
| 3% Pt/C, 70% wet | 2.00 g; 9.2 × 10$^{-5}$ g-atoms |
| dimethyl sulfoxide | 0.2 g; 0.00256 moles |
| dodecyltrimethylammonium chloride, 30% solution in isopropanol | 10 drops |

After charging was completed, the reactor was sealed, purged with nitrogen, purged with hydrogen and pressurized to 60 psig with hydrogen. The agitator was started and operated at a rapid rate causing the hydrogenation reaction to proceed. By application of cooling water through internal coils in the reactor the temperature was maintained at 15°–20° C. during the hydrogenation reaction. After approximately 0.45 moles hydrogen had been consumed, hydrogen flow was cut off and the reactor purged with nitrogen. The reactor was then disassembled and the entire reaction mixture placed in a 1 liter beaker under an inert atmosphere. The mixture was then heated to 85°–90° C. and held at that temperature for 30 minutes. Catalyst was then filtered out of the mixture and the filter cake washed with 50 ml toluene. The same aliquot of toluene was used to wash unreacted nitrobenzene from the filtered liquors.

The toluene washed PAP liquor was cooled to 10°–15° C. and ammonia added to a final pH of 7.5 to 8.0, thereby precipitating the PAP product. Dry product yield, compensated for PAP solubility losses, indicated a yield of 70% based on nitrobenzene consumed.

Approximately 88% of the nitrobenzene charge was converted.

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:

1. A process for production of substituted or unsubstituted p-aminophenol having the formula

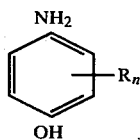

where R is lower alkyl and n is 0, 1 or 2, the process comprising the steps of:

preparing a charge mixture comprising a substrate selected from the group consisting of substituted and unsubstituted nitrobenzenes having the formula

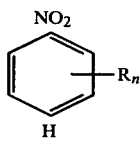

where R and n are as defined above, a catalyst containing platinum, and a sulfur compound selected from the group consisting of divalent sulfur compounds in which sulfur is bonded to two other moieties and compounds reducible to such divalent sulfur compounds under catalytic hydrogenation conditions;

introducing hydrogen into said mixture while agitating the mixture at a temperature in the range of between about 0° and about 40° C., thereby reducing said substrate to a hydroxylamine having the formula

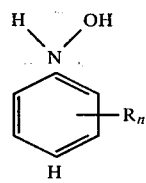

where R and n are as defined above; and thereafter heating said hydroxylamine to a temperature of at least about 70° C. and agitating it at at least about 70° C. in the presence of a highly dissociated acid, thereby effecting rearrangement of said hydroxylamine to the corresponding p-aminophenol.

2. A process as set forth in claim 1 wherein said charge mixture further contains said acid and comprises an aqueous phase containing said acid and an organic phase containing said substrate, the reduction of said substrate to said hydroxylamine is carried out in a hydrogenation vessel, the hydroxylamine product is absorbed into the aqueous phase as a salt of said acid, the aqueous phase is separated from the organic phase and transferred to a second reaction vessel, and the aqueous phase is heated to at least about 70° C., said rearrangement taking place in said second vessel at a temperature of at least about 70° C.

3. A process as set forth in claim 1 wherein said charge mixture further comprises a base and a solvent, said base being selected from the group consisting of ammonia, aliphatic amines, phosphite esters, phosphine, aliphatic phosphines and aryl phosphines, said solvent being selected from the group consisting of alcohols, ethers and esters, the solvent is stripped from the hydrogenation reaction mixture after the reduction reaction is terminated, and the hydroxylamine is thereafter contacted with said acid.

4. A process as set forth in claim 3 wherein said charge mixture comprises between about 100 and about 300 moles of said base per gram atom of platinum.

5. A process as set forth in claim 2 or 3 wherein said sulfur compound is selected from the group consisting of organic sulfides, organic disulfides, organic sulfoxides, hydrogen sulfide, thiols and thiophene.

6. A process as set forth in claim 5 wherein said sulfur compound is selected from the group consisting of dialkyl sulfoxides and aryl alkyl sulfoxides.

7. A process as set forth in claim 6 wherein said sulfur compound comprises a dialkyl sulfoxide and said mixture contains between about 150 and about 400 moles of said dialkyl sulfoxide per gram atom of platinum.

8. A process as set forth in claim 5 wherein said sulfur compound is selected from the group consisting of dialkyl sulfides, aryl alkyl sulfides, hydrogen sulfide and thiols.

9. A process as set forth in claim 8 wherein said sulfur compound comprises a dialkyl sulfide and said charge mixture contains between about 0.5 and about 20 moles of said dialkyl sulfide per gram atom of platinum.

10. A process as set forth in claim 3 wherein there is a maximum catalyst selectivity at an optimum locus of combinations of sulfur compound content and base content, and the process is controlled by incorporating sulfur compound in the charge mixture at a level lower than the optimum sulfur compound content at zero base content, and adjusting the base content to provide a combination on or near said locus.

11. A process as set forth in claim 10 wherein said sulfur compound is dimethyl sulfoxide and said base is ammonia the dimethyl sulfoxide is incorporated in the charge mixture at between 200 and 260 moles per gram atom of platinum, and the ammonia level is adjusted to between about 50 and about 300 moles per gram atom of platinum.

12. A process as set forth in claim 5 wherein said mixture contains between about $3.0 \times 10^{-5}$ and about $5.0 \times 10^{-4}$ gram-atoms platinum per mole of said substrate.

13. A process as set forth in claim 1 wherein said acid is selected from the group consisting of sulfuric acid, phosphoric acid, alkylsulfonic acids, arylsulfonic acids and trihaloacetic acids.

14. A process as set forth in claim 13 wherein said acid comprises sulfuric acid and has a strength of between about 5 and about 20% by weight.

15. A process as set forth in claim 14 wherein said acid has a strength of between about 10 and about 15% by weight.

16. A process as set forth in claim 1 wherein said sulfur compound comprises dimethyl sulfoxide.

17. A process as set forth in claim 1 wherein said sulfur compound is selected from the group consisting of dimethyl sulfide, ethyl propyl sulfide, bis(dodecyl) sulfide, and methyl octyl sulfide.

18. A process for production of substituted or unsubstituted p-aminophenol having the formula

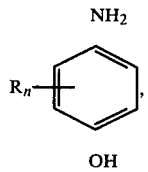

where R is lower alkyl and n is 0, 1 or 2, the process comprising the steps of:
preparing a charge mixture comprising a substrate selected from the group consisting of substituted and unsubstituted nitrobenzenes having the formula

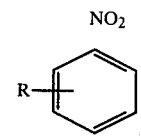

where R and n are as defined above, a catalyst containing platinum, and a sulfur compound selected from the group consisting of divalent sulfur compounds in which sulfur is bonded to two other moieties and compounds reducible to such divalent sulfur compounds under catalytic hydrogenation conditions;
introducing hydrogen into said mixture while agitating the mixture at a temperature in the range of between about 15 and about 20° C., thereby reducing said substrate to a hydroxylamine having the formula

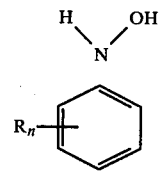

where R and n are as defined above; and
thereafter heating said hydroxylamine to a temperature of at least about 70° C. and agitating it at least about 70° C. in the presence of a highly dissociated acid, thereby effecting rearrangement of said hydroxylamine to the corresponding p-aminophenol.

* * * * *